(12) United States Patent
Kleingeld et al.

(10) Patent No.: US 8,268,941 B2
(45) Date of Patent: Sep. 18, 2012

(54) PROCESS FOR POLYMERISING OR OLIGOMERISING A HYDROCARBON

(75) Inventors: Anton Kleingeld, Johannesburg (ZA);
Craig McGregor, Sasolburg (ZA);
Richard Walsh, Vanderbijlpark (ZA)

(73) Assignee: Sasol Technology (Proprietary) Limited, Johannesburg (ZA)

( * ) Notice: Subject to any disclaimer, the term of this patent is extended or adjusted under 35 U.S.C. 154(b) by 111 days.

(21) Appl. No.: 12/741,832

(22) PCT Filed: Oct. 29, 2008

(86) PCT No.: PCT/IB2008/054456
§ 371 (c)(1),
(2), (4) Date: May 7, 2010

(87) PCT Pub. No.: WO2009/060342
PCT Pub. Date: May 14, 2009

(65) Prior Publication Data
US 2010/0249343 A1  Sep. 30, 2010

(30) Foreign Application Priority Data

Nov. 7, 2007  (ZA) ................................ 2007/09598
Nov. 7, 2007  (ZA) ................................ 2007/09600

(51) Int. Cl.
*C08F 2/00*     (2006.01)
*C08F 210/00*   (2006.01)
*B01J 19/00*    (2006.01)

(52) U.S. Cl. .............. 526/64; 526/68; 526/75; 526/348; 422/131

(58) Field of Classification Search .................... 526/64, 526/68, 75, 348; 422/131
See application file for complete search history.

(56) References Cited

FOREIGN PATENT DOCUMENTS

| | | |
|---|---|---|
| EP | 0 608 707 A1 | 8/1994 |
| EP | 1 777 000 A1 * | 4/2007 |
| JP | 10 045638 A | 2/1998 |
| WO | 2004/056479 A | 7/2004 |

* cited by examiner

*Primary Examiner* — William Cheung
(74) *Attorney, Agent, or Firm* — Baker & Hostetler LLP

(57) ABSTRACT

A process for polymerizing or oligomerising a hydrocarbon includes feeding at a low level a liquid hydrocarbon reactant into a bulk liquid phase comprising polymeric or oligomeric product admixed with a catalyst. The liquid hydrocarbon reactant is allowed to vaporise to form bubbles rising through the bulk liquid phase and to polymerise or oligomerise to form the polymeric or oligomeric product, with the rising bubbles creating turbulence in the bulk liquid phase, thereby mixing the bulk liquid phase. Gaseous components comprising any unreacted vaporised hydrocarbon reactant and any gaseous product that may have formed are withdrawn from a head space above the bulk liquid phase. Liquid phase from the bulk liquid phase is withdrawn to maintain the bulk liquid phase at a desired level.

16 Claims, 7 Drawing Sheets

US 8,268,941 B2

PROCESS FOR POLYMERISING OR OLIGOMERISING A HYDROCARBON

CROSS-REFERENCE TO RELATED APPLICATIONS

This application is a National Stage of International Patent Application No. PCT/IB2008/054456, filed on Oct. 29, 2008, which claims priority to foreign Patent Application No. ZA 2007/09598, filed on Nov. 7, 2007, and foreign Patent Application No. ZA 2007/09600, filed on Nov. 7, 2007, the disclosures of which are incorporated herein by reference in their entirety.

FIELD OF THE INVENTION

THIS INVENTION relates to the polymerising or oligomerising of a hydrocarbon. In particular, the invention relates to a process for polymerising or oligomerising a hydrocarbon, and to a hydrocarbon polymerisation or oligomerisation reactor.

BACKGROUND OF THE INVENTION

Many reaction processes exhibit fouling characteristics. Examples of such reaction processes are conventional polymerisation processes, including the oligomerisation, e.g. tetramerisation or trimerisation of olefins such as ethylene and/or propylene. The fouling of a reactor used in polymerisation reactions is manifested in the building up of a polymer film on an interior surface of a reactor wall and/or on other exposed metal surfaces such as injectors, nozzles, reactor internals and the like. This problem is particularly severe when the surfaces being fouled are at a temperature below the melting point of the polymer. The Applicant has found that this problem is also particularly prevalent on the ethylene injector nozzle and bottom dish of a reactor in which ethylene is tetramerised, with a mound of polymer building up on the bottom dish of the reactor.

A process for polymerising or oligomerising a hydrocarbon and a hydrocarbon polymerisation or oligomerisation reactor, which are less prone to fouling problems and improve heat removal, will be advantageous.

SUMMARY OF THE INVENTION

According to one aspect of the invention, there is provided a process for polymerizing or oligomerising a hydrocarbon, the process including feeding at a low level a liquid hydrocarbon reactant into a bulk liquid phase comprising polymeric or oligomeric product admixed with a catalyst;

allowing the liquid hydrocarbon reactant to vapourise to form bubbles rising through the bulk liquid phase and to polymerise or oligomerise to form the polymeric or oligomeric product, with the rising bubbles creating turbulence in the bulk liquid phase, thereby mixing the bulk liquid phase;

allowing gaseous components comprising any unreacted vapourised hydrocarbon reactant and any gaseous product that may have formed to disengage from the bulk liquid phase into a head space above the bulk liquid phase;

withdrawing the gaseous components from the head space; and withdrawing liquid phase from the bulk liquid phase, to maintain the bulk liquid phase at a desired level.

The liquid hydrocarbon is thus typically fed at or near a bottom of a reactor containing a bubbling column of the bulk liquid phase.

The process may include cooling the gaseous components withdrawn from the head space, forming condensed hydrocarbon reactant and gaseous product. The condensed hydrocarbon reactant may be separated from the gaseous product. The condensed hydrocarbon reactant may be recycled in liquid form to the bulk liquid phase.

The bulk liquid phase may include an inert solvent, e.g. to act as a diluent thereby limiting incorporation of desirable oligomeric product in lower value or heavier by-products. Any inert solvent that does not react with components of the bulk liquid phase, and which does not crack in the temperature range 25 to 300° C. can be used. These inert solvents may include saturated aliphatics, unsaturated aliphatics, aromatic hydrocarbons and halogenated hydrocarbons. Typical solvents include, but are not limited to, benzene, toluene, xylene, cumene, heptane, methylcyclohexane, methylcyclopentane, cyclohexane, Isopar C, Isopar E, 2,2,4-trimethylpentane, Norpar, chlorobenzene, 1,2-dichlorobenzene, ionic liquids and the like.

The process may include treating the gaseous product to recover uncondensed unreacted hydrocarbon reactant from the gaseous product. This treatment may include at least one distillation stage operating at a lower pressure than the pressure at which the bulk liquid phase is maintained, producing the hydrocarbon reactant in liquid form.

The process may include treating the withdrawn liquid phase to separate polymeric or oligomeric product from solvent. The treatment of the liquid phase may include subjecting the liquid phase to at least one distillation stage to obtain a solvent stream.

The polymerisation or oligomerisation reaction or reactions in the bulk liquid phase may be exothermic. Sufficient liquid hydrocarbon reactant may be fed to the bulk liquid phase to balance the reaction exotherm, thereby approaching isothermal behaviour, i.e. maintaining a steady temperature in the bulk liquid phase. This feature of the invention may in some embodiments of the invention be important, as the absence of a heat exchanger in direct contact with the bulk liquid phase reduces the surface area that may be susceptible to fouling, which is often a problem with polymerisation or oligomerisation processes. Furthermore, in one embodiment of the invention, the vigorous mixing caused by the vapourisation of liquid droplets of the hydrocarbon reactant as it enters the bulk liquid phase to form rising gas bubbles obviates the need for a stirrer or agitator, which may also be susceptible to fouling.

The liquid hydrocarbon reactant may be an olefins feedstock, i.e. comprising one or more olefinic monomers. Preferably, the olefins feedstock comprises predominantly α-olefins, e.g. ethylene.

The process may thus be an oligomerisation process. In one embodiment of the invention, the process is predominantly a trimerisation process. In another embodiment of the invention, the process is predominantly a tetramerisation process.

In a further embodiment, the process is predominantly both a trimerisation process and a tetramerisation process.

The liquid hydrocarbon reactant may thus be liquid ethylene. The liquid hydrocarbon reactant is preferably sub-cooled. The degree of sub-cooling is preferably sufficient to prevent premature flashing of the liquid hydrocarbon in a feed line and/or nozzle used to feed the liquid hydrocarbon into the bulk liquid phase. In one embodiment of the invention, in which the liquid hydrocarbon is liquid ethylene, the liquid ethylene is at a temperature of about −5 to +7° C., most preferably at a temperature of between 0 and 4° C. The liquid ethylene may however be at a temperature of between about −30 to +9° C.

When the liquid hydrocarbon reactant is liquid ethylene, the bulk liquid phase may be at an operating pressure of at least about 1 bar(g), more preferably at least about 10 bar(g), most preferably at least about 30 bar(g), e.g. about 45 bar(g). The temperature of the bulk liquid phase may be from 30 to 100° C., preferably from 40 to 80° C. This temperature is typically below the boiling temperature of the bulk liquid phase, but above the boiling temperature of the liquid hydrocarbon reactant.

The trimerisation of ethylene to 1-hexene is a significant commercial operation. In addition to its use as a specific chemical, 1-hexene is extensively used in polymerisation processes either as a monomer or co-monomer. The trimeric products derived from longer chain olefins can be used as synthetic lubricants (e.g. as polyalphaolefins) and in applications such as components of drilling muds and as a feedstock to prepare detergents and plasticizers.

In one embodiment of the invention, the catalyst is a dissolved transition metal compound catalyst, e.g. a chromium catalyst, with a heteroatomic or homoatomic, ligand, typically used with an activator. A number of dissolved transition metal compound catalysts have been developed for use to trimerise or tetramerise olefins, e.g. as disclosed in U.S. Pat. No. 4,668,838; EP 0668105; U.S. Pat. No. 5,750,817; U.S. Pat. No. 6,031,145; U.S. Pat. No. 5,811,618; WO 03/053890; WO 2004/056478; WO 2004/056477; WO 2004/056479; WO 2004/056480; WO 2005/123633 and WO 2007/007272, all of which are incorporated herein by reference. The catalyst may instead be a nickel catalyst comprising a chelating ligand, e.g. 2-diphenyl phosphine benzoic acid, typically used with a catalyst activator such as sodium tetraphenylborate. Also possible is the use of trialkylaluminium catalysts.

Some of these catalysts are selective for $C_6$ and $C_8$ oligomeric products, e.g. 1-hexene and 1-octene, and the Applicant believes that such catalysts will be particularly advantageous for use with the process of the invention as the selective production of 1-hexene and 1-octene is commercially important.

Suitable activators include organoaluminium compounds, boron compounds, organic salts, such as methyl lithium and methyl magnesium bromide, inorganic acids and salts, such as tetrafluoroboric acid etherate, silver tetrafluoroborate, sodium hexafluoroantimonate, aluminate activators e.g. trityl perfluoro-tributyl aluminate, and the like.

Organoaluminium compounds which act as suitable activators include alkylaluminium compounds such as trialkylaluminium and aluminoxanes.

Aluminoxane activators are well known in the art and can be prepared by the controlled addition of water to an alkylaluminium compound, such as trimethylaluminium. In such process the alkylaluminium compounds are only partially hydrolysed to prevent or at least to reduce the formation of aluminium hydroxide during the preparation of aluminoxanes. Commercially available aluminoxanes consequently include unreacted alkylaluminium. The result is that commercially available aluminoxanes are usually mixtures of an aluminoxane and an alkylaluminium.

In this specification the term "aluminoxanes" is used to denote a compound represented by the general formulae $(R^a—Al—O)_n$ and $R^b(R^c—Al—O)_n—AlR^d{}_2$ wherein $R^a$, $R^b$, $R^c$, and $R^d$ are independently a $C_1$-$C_{30}$ alkyl or halo-alkyl radical, for example methyl, ethyl, propyl, butyl, 2-methyl-propyl, pentyl, isopentyl, neopentyl, cyclopentyl, hexyl, isohexyl, cyclohexyl, heptyl, octyl, iso-octyl, 2-ethyl-hexyl, decyl, 2-phenyl-propyl, 2-(4-fluorophenyl)-propyl, 2,3-dimethyl-butyl, 2,4,4-timethyl-pentyl and dodecyl; and n has the value of 2 to 50. Preferably n is at least 4.

In one embodiment of the invention the oligomerisation catalyst includes a combination of
i) a source of Cr; and
ii) a ligating compound of the formula

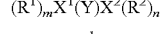

wherein: $X^1$ and $X^2$ are independently selected from the group consisting of
N, P, As, Sb, Bi, O, S and Se;
Y is a linking group between $X^1$ and $X^2$;
m and n are independently 0, 1 or a larger integer; and
$R^1$ and $R^2$ are independently hydrogen, a hydrocarbyl group or a heterohydrocarbyl group, and $R^1$ being the same or different when m>1, and $R^2$ being the same or different when n>1.

In this specification a heterohydrocarbyl group is a hydrocarbyl group which includes at least one heteroatom (that is not being H or C), and which organic compound binds with one or more other moieties through one or more carbon atoms of the organic compound and/or one or more heteroatoms of the organic compound. Organoheteryl groups and organyl groups (which include at least one heteroatom) are examples of heterohydrocarbyl groups.

Preferably the ligating compound is of the formula

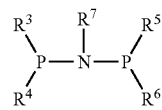

with $R^3$ to $R^7$ as defined above.

Preferably each of $R^3$ to $R^6$ is an alkyl (preferably methyl, ethyl or isopropyl) or aromatic (preferably phenyl or substituted phenyl).

Non limiting examples of the ligating compound are
(phenyl)$_2$PN(propyl)P(phenyl)$_2$;
(phenyl)$_2$PN(cyclopentyl)P(phenyl)$_2$;
(phenyl)$_2$PN(isopropyl)P(phenyl)$_2$;
(phenyl)$_2$PN((4-t-butyl)-phenyl)P(phenyl)$_2$;
(2-naphthyl)$_2$PN(methyl)P(phenyl)$_2$;
(2-methylphenyl)(phenyl)PN(isopropyl)P(2-methylphenyl)(phenyl);
(ethyl)(phenyl)P-1,2-benzene-P(ethyl)(phenyl);
(4-methoxyphenyl)$_2$PN(isopropyl)P(Phenyl)$_2$;
(2-methoxyphenyl)$_2$P-1,2-benzene-P(2-methoxyphenyl)$_2$
(phenyl)$_2$PN(1,2-dimethylpropyl)P(phenyl)$_2$;
(phenyl)$_2$PN(cyclopentyl)P(phenyl)$_2$; (phenyl)$_2$PN(cyclohexyl)P(phenyl)$_2$;
(phenyl)$_2$PN(1-adamantyl)P(phenyl)$_2$;
(phenyl)$_2$PN(2-adamantyl)P(phenyl)$_2$;
(phenyl)$_2$PN(S-Chipros)P(phenyl)$_2$;
(phenyl)$_2$P—N(methyl)-N-(isopropyl)P(phenyl)$_2$;
(phenyl)$_2$P—N(methyl)-N-(ethyl)P(phenyl)$_2$;
(phenyl)$_2$P—N(ethyl)-N-(ethyl)P(phenyl)$_2$;
(2-isopropylphenyl)$_2$PN(methyl)P(2-isopropylphenyl)$_2$ and
(2-methoxyphenyl)$_2$PN(methyl)P(2-methoxyphenyl)$_2$.

The process may include combining a gaseous hydrocarbon reactant feed with the gaseous components withdrawn from the head space, so that the gaseous hydrocarbon feed is condensed with the condensed hydrocarbon reactant and fed with the recycled condensed hydrocarbon reactant to the bulk liquid phase as the liquid hydrocarbon reactant.

The process may include treating the withdrawn liquid phase to separate unreacted hydrocarbon reactant from the polymeric or oligomeric product. This treatment may include subjecting the withdrawn liquid phase to at least one distillation stage and withdrawing the unreacted hydrocarbon reactant as an overhead stream from the distillation stage. The withdrawn unreacted hydrocarbon reactant may be recycled to the bulk liquid phase.

The liquid hydrocarbon reactant being fed into the bulk liquid phase may be impinged on an impingement surface provided in a reactor holding the bulk liquid phase, or on another feed stream entering the reactor, to create at least a localised area of high turbulence in the bubbling bulk liquid phase.

The liquid hydrocarbon reactant feed being impinged on an impingement surface provided in the reactor, or on another feed stream entering the reactor, may also create turbulence in the bulk of the liquid phase. Preferably, a volume of the bulk liquid phase in which such localised turbulence is created by the impingement of feed streams includes inlet nozzles for said feed streams. As will be appreciated, being located in a volume of localised turbulence, the nozzles are less prone to fouling.

The liquid hydrocarbon reactant may be impinged against an impingement surface defined by a wall of the reactor. The wall of the reactor may be a side wall or a floor or bottom dish of the reactor. In one embodiment of the invention, the impingement surface is defined by a floor or bottom dish of the reactor. Instead, or in addition, the liquid hydrocarbon reactant may be impinged against an impingement formation provided inside the reactor, defining an impingement surface. When the liquid hydrocarbon reactant feed is being impinged on another feed stream entering the reactor, said another feed stream may also be a liquid hydrocarbon reactant feed.

The impingement surface, e.g. a bottom dish of the reactor, may be heated. It is not necessary to heat the impingement surface above the melting point of the polymeric or oligomeric product. A surface temperature of the impingement surface may be between about 80 and about 200° C., e.g. between about 90 and about 115° C.

The liquid hydrocarbon reactant may be fed into the bulk liquid phase through at least one nozzle aimed at the impingement surface. Preferably, the liquid hydrocarbon reactant is fed into the bulk liquid phase through a plurality of nozzles aimed at the impingement surface.

The nozzle or nozzles may be heated, e.g. with a steam or condensate jacket, with a hot solvent loop, or electrically. The nozzle or nozzles may be heated to have a surface temperature ranging between about 80 and about 200° C., e.g. between about 90 and about 140° C.

As will be appreciated, the maximum spacing between a nozzle and the impingement surface that will still allow effective creation of a localised area of high turbulence will depend at least on the injection velocity of the liquid hydrocarbon reactant, with a larger spacing being tolerated for higher injection velocities.

The process may include feeding the liquid phase withdrawn from the bulk liquid phase to a further bubbling column of said bulk liquid phase, and feeding said liquid hydrocarbon reactant also to said further bubbling column, to form further polymeric or oligomeric product. In other words, the process may use at least two bubbling columns of bulk liquid phase in series, with fresh liquid hydrocarbon reactant being fed into each bubbling column, e.g. to impinge on an impingement surface or on another feed stream entering the bulk liquid phase (i.e. the bubbling columns are in parallel for the liquid hydrocarbon reactant), and preferably with the withdrawn gaseous components from the head spaces above the bubbling columns being combined.

According to another aspect of the invention, there is provided a hydrocarbon polymerisation or oligomerisation reactor which includes:
- a reactor vessel defining a liquid phase zone below a head space zone for holding a bulk liquid phase comprising polymeric or oligomeric product in the liquid phase zone;
- a hydrocarbon reactant inlet at a low level leading into the liquid phase zone, the inlet having at least one hydrocarbon reactant inlet nozzle aimed at an impingement surface provided inside, or defining, the liquid phase zone such that in use a localised area of high turbulence is created by the injection of a hydrocarbon reactant through the hydrocarbon reactant inlet nozzle onto the impingement surface, or said at least one hydrocarbon reactant inlet nozzle being aimed at another fluid stream inlet nozzle so that in use a localised area of high turbulence is created by the injection of a hydrocarbon reactant through said at least one hydrocarbon reactant inlet nozzle into impinging contact with a fluid stream being injected through said another fluid stream inlet nozzle; and
- a gaseous components outlet leading from the head space zone in use through which gaseous components collecting in the head space zone are withdrawn.

Each nozzle may have a plurality of holes configured to direct a jet of liquid to impinge a surface. The angle of incidence of the impinging jets to the surface can either be the same for all holes or could differ for the holes.

The hydrocarbon reactant inlet may include a plurality of hydrocarbon reactant inlet nozzles each aimed at an impingement surface, or at another fluid stream inlet nozzle. Said another fluid stream inlet nozzle may be a hydrocarbon reactant inlet nozzle.

The impingement surface may be defined by a wall of the reactor. The wall of the reactor may be a side wall or a floor or bottom dish of the reactor. In one embodiment of the invention, the impingement surface is defined by a floor or bottom dish of the reactor. Instead, or in addition, the impingement surface may be defined by an impingement formation provided as an internal inside the liquid phase zone.

The reactor may be characterised by the absence of a mechanical stirrer or agitator.

The reactor may include a solvent inlet into the reactor vessel in use through which a solvent can be fed into the reactor vessel. The reactor my also include a catalyst inlet in use through which a catalyst or catalyst system can be fed in to the reactor vessel.

The reactor may be a bubble column reactor. Preferably, the reactor has no internals apart from the hydrocarbon reactant inlet nozzles. More particularly, the reactor may be a bubble column, $\alpha$-olefins oligomerisation reactor. In such a reactor, an exit velocity of 1.8 to 3 m/s may be used for hydrocarbon reactant leaving a nozzle, with the required pressure in an inlet line being determined by nozzle hole diameter and number of holes to deliver the desired exit velocity.

BRIEF DESCRIPTION OF THE DRAWINGS

The invention will now be described, by way of example, with reference to the accompanying drawings in which.

DETAILED DESCRIPTION

Figure 1:
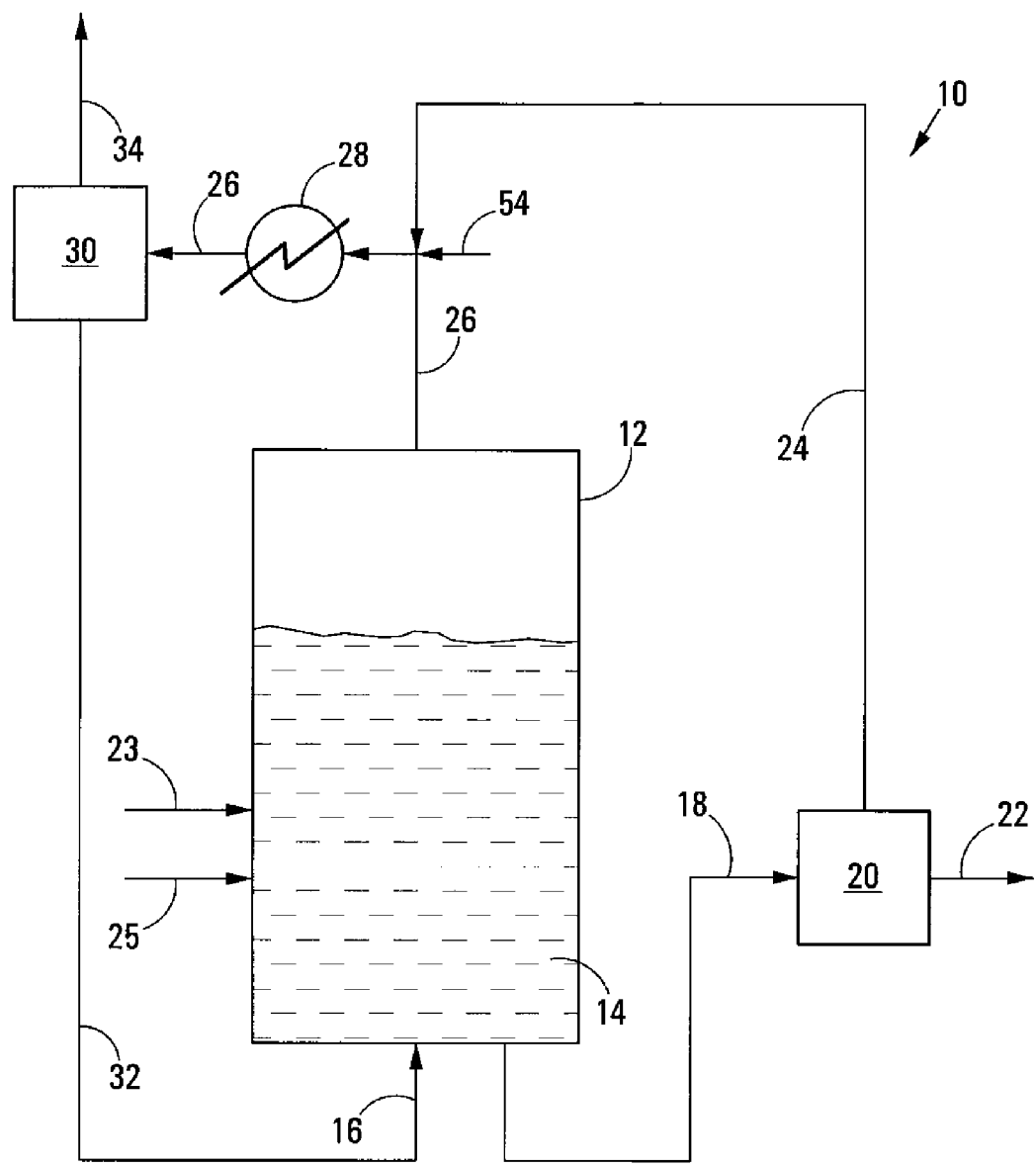
FIG. 1 shows one embodiment of a process in accordance with the invention for polymerising or oligomerising a hydrocarbon.

Referring to FIG. 1 of the drawings, reference numeral 10 generally indicates a process in accordance with the invention for polymerising or oligomerising a hydrocarbon. The process 10 as shown in the drawing is in particular for the tetramerisation, and to a lesser extent trimerisation, of ethylene but it can also be used for the polymerisation or oligomerisation of other olefins feedstocks.

The process 10 includes a reactor 12 containing a bulk liquid phase 14 in the form of a bubbling column. The reactor 12 is thus a bubbling column reactor. Liquid ethylene from a line 32 enters a bottom of the reactor 12 so that the liquid ethylene in use enters the bottom of the bubbling column of bulk liquid phase 14. A solvent line 23 and a catalyst line 25 also enter the reactor 12.

A liquid phase withdrawal line 18, preferably with a bottom withdrawal point leaves from the reactor 12 to a treatment stage 20, with an oligomeric product line 22 and an unreacted ethylene line 24 leaving the treatment stage 20. A gaseous components line 26 leaves from a top of the reactor 12 to a condenser 28 and leads from the condenser 28 to a separator 30. The unreacted ethylene line 24 from the treatment stage 20 joins the gaseous components line 26 leading into the condenser 28. A gaseous ethylene feed line 54 also joins the gaseous components line 26 leading into the condenser 28.

The line 32 is a liquid ethylene recycle line which leads from the separator 30 to the reactor 12, with a gaseous product line 34 also leading from the separator 30.

In order to trimerise and tetramerise ethylene to produce 1-hexene and 1-octene, liquid ethylene at a temperature of about 5° C. is fed by means of the line 32 into the bottom of the bulk liquid phase 14 inside the reactor 12. The reactor 12 is operated typically at a pressure of between about 45 bar(g) and 50 bar(g), with the bulk liquid phase 14 being at a temperature below its boiling point at the operating pressure of the reactor 12. Typically, this temperature is about 60° C.

The bulk liquid phase 14 of the bubbling column comprises an admixture of oligomeric products and a solvent which includes a dissolved catalyst system, with fast rising bubbles of vapourised ethylene passing upwardly through the bubbling column of bulk liquid phase 14. In the embodiment of the invention shown in FIG. 1, the solvent is a $C_8$ paraffin (Isopar-C), with the catalyst system comprising Cr (chromium), $(phenyl)_2PN(isopropyl)P(phenyl)_2$ ligand and methyl aluminoxane as activator.

The reactor 12 with the particular catalyst system primarily produces 1-hexene and 1-octene from ethylene. In other words, the reactor 12 primarily trimerises and tetramerises the ethylene. The oligomerisation reactions taking place inside the reactor 12 are exothermic. The heat of reaction is sufficient to provide the energy required to heat the incoming liquid ethylene feed from 5° C. to 60° C. and to vapourise the liquid ethylene. The vapourisation of the liquid ethylene and hence the formation of fast rising gas bubbles creates vigorous mixing inside the bulk liquid phase 14, turning the bulk liquid phase 14 into a bubbling column. This is important and advantageous, as it may allow the reactor 12 to operate without a stirrer or agitator, which, if present, may be susceptible to fouling. Temperature control of the reactor 12 is effected by means of flashing of liquid ethylene so there is no need for a heat exchanger in direct contact with the bulk liquid phase 14 to remove heat from the bulk liquid phase 14 (i.e. direct-contact cooling or so-called "hot cooling" is employed).

In general, ethylene oligomerisation processes form small quantities of solids and process designs are required that can handle this material. One solution is to design a catalyst or catalyst system which can be used at a temperature high enough to have the fouling polymer solids in solution, thereby to prevent fouling. Alternatively, if the operating temperature of the process is too low so that precipitation will occur, a conventional approach is to use an external heat exchanger to prevent contact of heat exchange surfaces and process fluids with the fouling polymers. With the process of the invention, a liquid hydrocarbon feed that has a boiling temperature lower than the bulk temperature of the liquid phase of the bubbling column at the reaction pressure is used so that, on contact with the bulk liquid phase, the liquid hydrocarbon will vapourise rapidly releasing bubbles that induce turbulence and generate sufficient mixing in the reactor. This can eliminate the requirement for an agitator and hence agitator fouling as a reason for plant shutdown, extending run times and increasing plant availability and hence reducing the need for increased plant size to meet capacity requirements. Given that phase change results in a large change in density for a given mass of liquid hydrocarbon fed into the reactor, a significant amount of work can be carried out on the bulk liquid phase bubbling column by vapourising the liquid hydrocarbon stream in the bulk liquid phase, while maintaining an isothermal reaction environment. Given that a fouling process such as a tetramerisation process requires periodic cleaning, the fact that an agitator may not be needed to maintain good mixing under reaction conditions allows a more tailored design to be implemented to allow for optimisation of a reactor cleaning step.

The liquid phase is withdrawn through the liquid phase withdrawal line 18 to maintain the bulk liquid phase 14 at a desired level within the reactor 12. A catalyst kill reagent, e.g. an alcohol such as ethanol, may be introduced to the withdrawn liquid product stream to prevent further reaction. The liquid phase is treated in the treatment stage 20, providing an unreacted gaseous ethylene stream which is withdrawn along line 24 and thus returned in liquid form to the reactor 12 together with fresh ethylene fed by means of the line 54, via the condenser 28, separator 30 and the recycle line 32. An oligomeric product is withdrawn from the treatment stage 20 by means of the oligomeric product line 22. In FIG. 1, the treatment stage 20 is represented by a single block. In practice, the separation of unreacted ethylene (and polymer solids that may have formed) from the liquid phase requires a complex series of separation steps typically including at least one distillation or flash stage and possibly one compression stage. As the recovery of unreacted ethylene from the liquid product is however peripheral to the present invention, this will not be discussed in any more detail.

The process 10 will typically also include recovering the solvent from the oligomeric product. The solvent is then returned to the reactor 12 by means of the solvent line 23. Recovery is typically effected using a distillation column, but the details of this recovery are also not required for an understanding of the present invention and will not be discussed in any detail.

Gaseous components, including unreacted vapourised ethylene and any gaseous product that may have formed in the reactor 12, are collected in a headspace above the bulk liquid phase 14 and withdrawn through the gaseous components line 26. The gaseous components may also include light impurities, such as methane, which may have entered the process 10 with the liquid ethylene feed and ethane formed in the reactor 12 as a by-product. Methane may also be liberated in a catalyst deactivation reaction, particularly when the catalyst includes an aluminium specie, as a result of the reaction of an alcohol with the aluminium specie. The partial pressure of light impurities, e.g. methane and ethane, in the reactor 12 should be minimised as far as practically possible, to increase the ethylene partial pressure thereby increasing the ethylene concentration in the bulk liquid phase 14, and hence increasing the productivity of the reactor 12.

In the condenser 28, the gaseous components withdrawn along the gaseous components line 26 are cooled, forming condensed ethylene which is knocked out in the separator 30 and returned to the reactor 12 by means of the liquid ethylene recycle line 32.

Uncondensed gaseous components, i.e. gaseous product, are withdrawn from the separator 30 by means of the gaseous product line 34. Although not shown in FIG. 1 of the drawings, the process 10 may include treating the gaseous product withdrawn by means of the gaseous product line 34 to recover uncondensed unreacted ethylene from the gaseous product. Typically, such a treatment will include at least one distillation stage operating at a lower pressure and a lower temperature than the reactor 12, producing liquid ethylene which can be pumped back to the reactor 12.

Naturally, the process 10 may include treating the oligomeric product from the treatment stage 20 to separate desired components, such as 1-hexene, 1-octene, a cyclic $C_6$ product and a $C_{10}+$ product and solvent. Such separation will typically take place in distillation columns.

Figure 2:
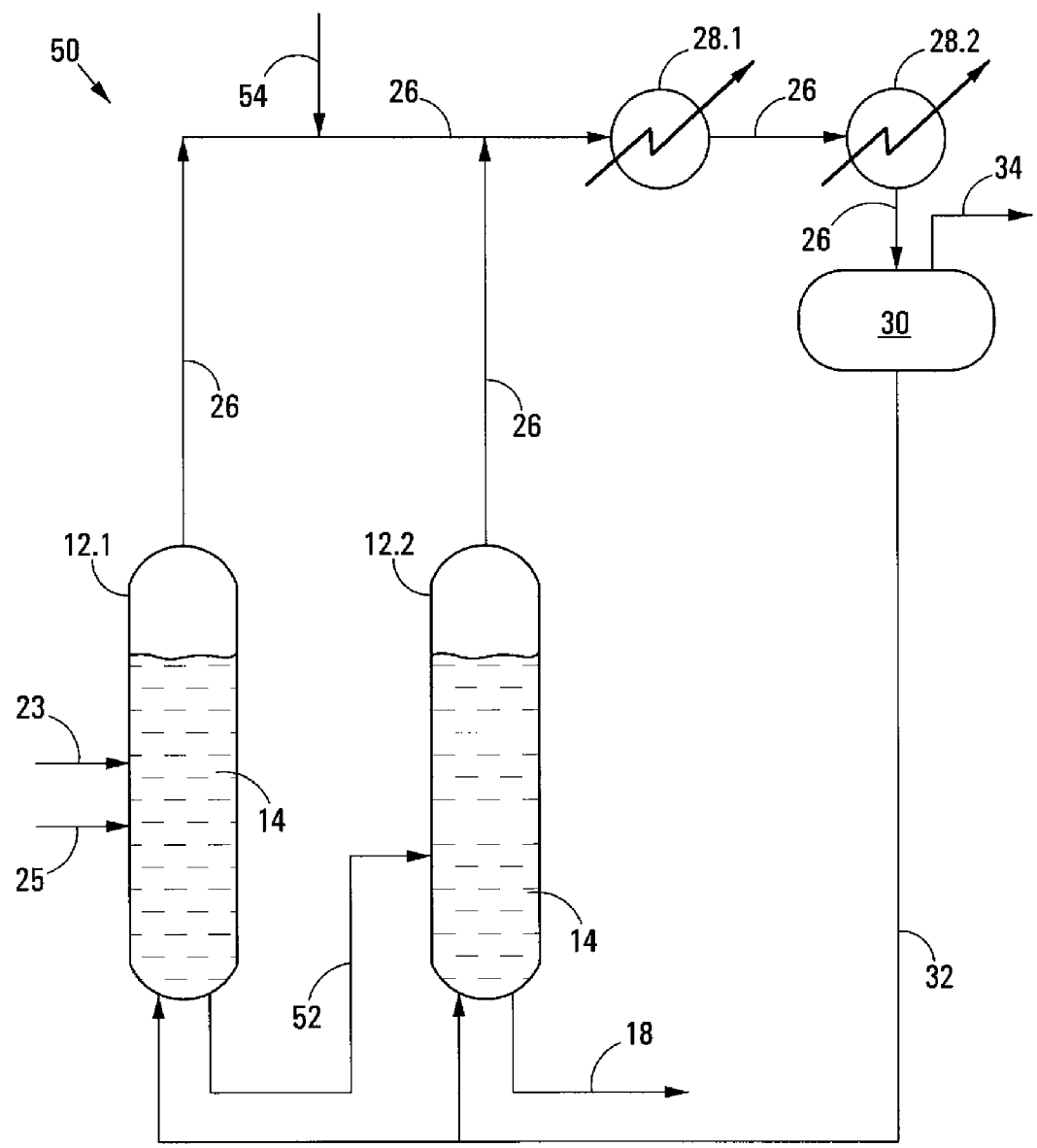
FIG. 2 shows another, more complex embodiment of a process in accordance with the invention for polymerising or oligomerising a hydrocarbon.

Referring to FIG. 2 of the drawings, a more complex embodiment of the process in accordance with the invention is generally indicated by reference numeral 50. In FIG. 2, the same reference numerals have been used as far as possible as have been used in FIG. 1 to indicate the same or similar parts or features.

The process 50 includes two reactors 12.1 and 12.2. Instead of a single condenser, the process 50 includes two heat exchangers 28.1 and 28.2. The reactors 12.1 and 12.2. are in series as far as the bulk liquid phase 14 is concerned and a liquid phase transfer line 52 is thus provided to transfer liquid phase from the reactor 12.1 to the reactor 12.2. As far as the liquid ethylene feed is concerned, the reactors 12.1 and 12.2 are however in parallel so that liquid ethylene feed lines 16 enter both reactors 12.1 and 12.2 at their bottoms.

The process 50 receives feed ethylene in compressed gaseous form along the gaseous ethylene feed line 54. The fresh gaseous ethylene feed is combined with the gaseous components withdrawn by means of the gaseous components lines 26 from the reactors 12.1 and 12.2. In the first heat exchanger 28.1, this combined gaseous stream is first cooled from about 60° C. to about 40° C. using plant cooling water, and in the second heat exchanger 28.2 the combined gaseous stream is further cooled to about 7° C. using refridged water or any other appropriate refrigerant at about 0° C. Condensed liquid ethylene is then fed to the reactors 12.1 and 12.2 from the separator 30. In the process 50, this liquid ethylene feed stream includes recycled liquid ethylene and fresh liquid ethylene.

Liquid phase is transferred from the reactor 12.1 to the reactor 12.2 by means of the liquid phase transfer line 52 (where the impetus for transfer is provided by a difference in pressure between reactors 12.1 and 12.2), before being withdrawn by means of the liquid phase withdrawal line 18. Liquid ethylene is however fed in parallel by means of the liquid ethylene feed line 16 into the bottoms of the reactors 12.1 and 12.2.

Although not shown in FIG. 2, the process 50 may naturally include a treatment stage such as the treatment stage 20 to recover unreacted ethylene from the liquid phase withdrawn by means of the liquid phase withdrawal line 18, as well as further treatment stages to recover and recycle solvent and to recover unreacted ethylene from the gaseous product withdrawn by means of the gaseous product line 34.

The Applicant has performed cold model experiments on a vapourising butane system to understand the effects of rapid vapourisation on bulk mixing and circulation. The butane system consisted of a water-filled 10-liter glass vessel with an inside diameter of 20 cm, into which sub-cooled liquid butane was fed through a single quarter inch tube. A colour (potassium permanganate) tracer was added to highlight flow patterns and local velocities.

When the butane was simply fed into the water, it was clear that all of the butane immediately bubbled upwards in a plume from the injector, imparting very little mixing to the liquid below that point. Zones outside of the plume of rising butane showed low flow and low turbulence. Distinct zones of high and low mixing could be discerned inside the reactor, evidenced by the absence of bubbles in the low flow regions. This has been confirmed by results of CFD simulation. These phenomena explain the behaviour of a tetramerisation piloting reactor operated by the Applicant, where excessive polymer build-up on the bottom dish is believed to be due to low turbulence under the ethylene injector entering the pilot scale reactor from the side.

When the butane injector was arranged so that injected butane impinges against a bottom dish of the glass vessel, low flow regions were eliminated and even dissipation of energy in the bulk of the water was promoted, as evidenced by a more uniform bubble size distribution throughout the liquid. The liquid bulk appeared murky, indicative of fine bubbles distributed throughout the liquid. This suggests that careful consideration should be given to the manner in which the liquid ethylene is fed into the bubbling column of bulk liquid phase to ensure even distribution of ethylene bubbles throughout the bulk liquid phase, when the process of the invention is employed.

Figure 5:
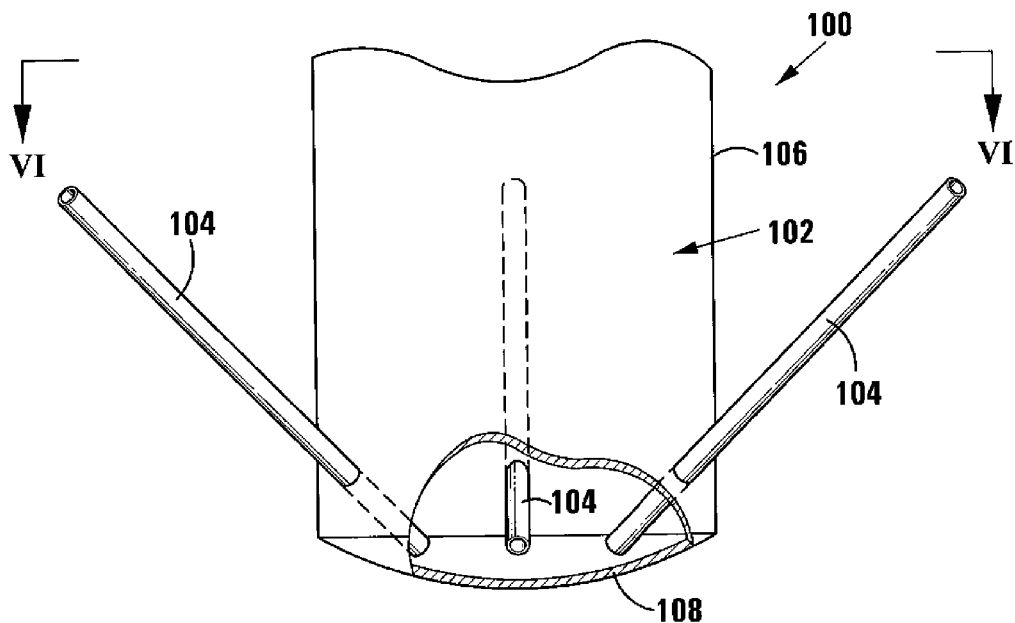
FIG. 5 shows a partially sectioned elevational view of a bottom portion of a hydrocarbon oligomerisation reactor in accordance with the invention.
Figure 6:
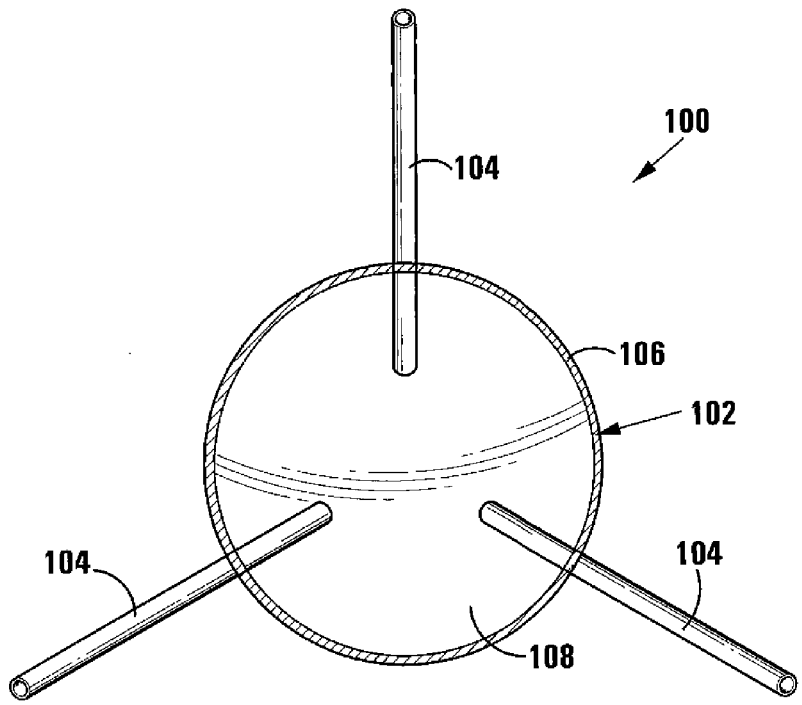
FIG. 6 shows a sectioned top view of the reactor of FIG. 5, taken at VI-VI in FIG. 5.

Referring to FIGS. 5 and 6 of the drawings, an oligomerisation reactor in accordance with the invention is generally indicated by reference numeral 100. The reactor 100 includes a reactor vessel 102 and a hydrocarbon reactant inlet comprising three nozzles 104 passing through a circular cylindrical side wall 106 of the reactor vessel 102.

Although not shown in the drawing, most of the vessel 102 defines a bulk liquid phase zone extending from a bottom dish 108 upwardly to take up 70% to 90% of the volume of the reactor vessel 106. A top portion of the reactor vessel 102 defines a head space zone. A gaseous components outlet (not shown) leads from the head space zone.

The nozzles 104 are directed towards the bottom dish 108, with the outlet of each nozzle 104 being spaced any distance from a few millimeters to a few centimeters from the bottom dish, where this distance between nozzle and dish is determined in practice by the velocity of the fluid jet exiting the nozzle.

Although also not shown in FIGS. 5 and 6 of the drawings, the reactor 100 includes a solvent inlet and a catalyst system inlet through the side wall 106, into the liquid phase zone. A liquid phase withdrawal line to withdraw liquid phase from the reactor 100 is also provided (not shown).

Apart from the nozzles 104 projecting through the side wall 106, the reactor 100 will preferably not have any internals and in particular may not require a mechanical stirrer or agitator.

The reactor 100 is a bubble column, α-olefins oligomerisation reactor and is particularly suitable for tetramerising or trimerising a liquid ethylene feed. In use, the bulk liquid phase zone of the reactor vessel 102 is filled with a bulk liquid phase comprising polymeric or oligomeric product, e.g. 1-hexene and/or 1-octene in admixture with a solvent and a dissolved catalyst or catalyst system. When the reactor 100 is used in the process 10, 50 (i.e. as the reactors 12, 12.1 and 12.2) the bulk liquid phase is in the form of a bubbling column, with the reactor operating at a pressure of between about 45 bar(g) and about 50 bar(g). The bubbling column is thus at a temperature below the boiling temperature of the bulk liquid phase at the operating pressure of the reactor, typically about 60° C.

Liquid ethylene, at a temperature of about 5° C., is fed into the reactor vessel 102 through the nozzles 104 to impinge against the bottom dish 108. This produces localised areas of high turbulence in the immediate vicinity of the bottom dish 108, which reduces fouling of the bottom dish 108 or the nozzles 104 with a polymer film. In addition, turbulence in the bulk of the liquid phase in the liquid phase zone is also increased. Furthermore, the vapourisation of the liquid ethylene and hence the formation of fast rising gas bubbles also creates vigorous mixing ensuring that the bulk liquid phase is in the form of a bubbling.

Figure 7:
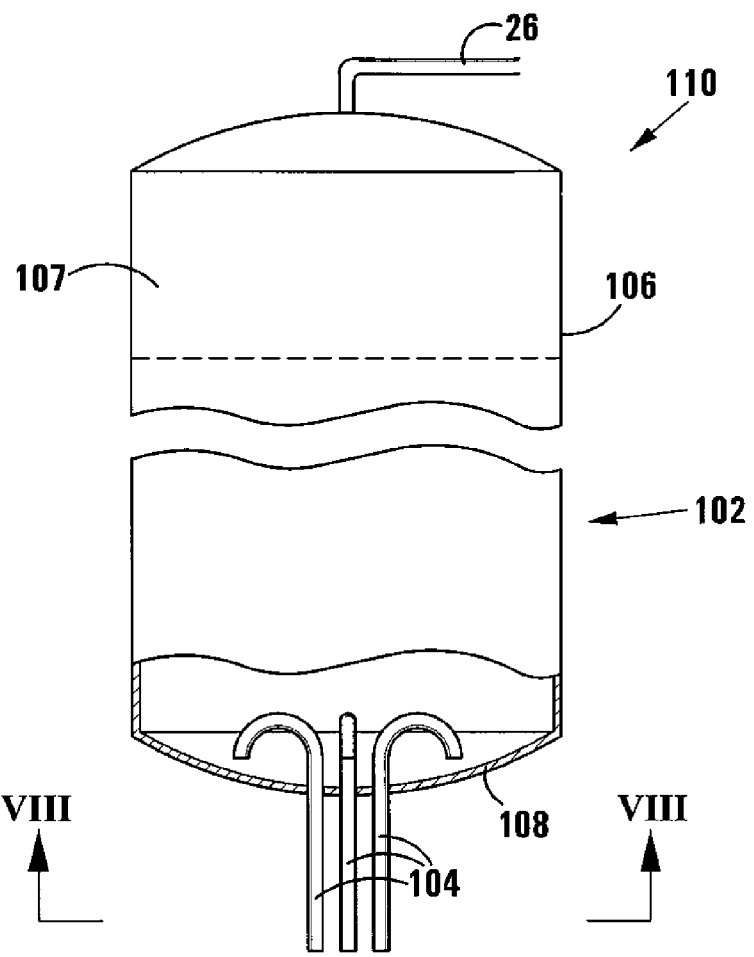
FIG. 7 shows a partially sectioned elevational view of another embodiment of an oligomerisation reactor in accordance with the invention.
Figure 8:
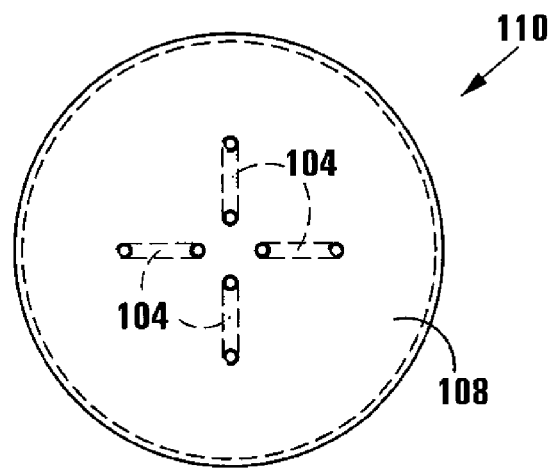
FIG. 8 shows a bottom view of the reactor of FIG. 7, taken at VIII-VIII in FIG. 7.

Referring to FIGS. 7 and 8, another embodiment of an oligomerisation reactor in accordance with the invention is generally indicated by reference numeral 110. The reactor 110 is similar to the reactor 100 and unless otherwise indicated, the same or similar parts or features are indicated by the same reference numerals.

In the reactor 110, the nozzles 104 enter the vessel 106 through the bottom dish 108 and then make a 180° turn to ensure that injected liquid hydrocarbon impinges against the bottom dish 108, in use. The configuration shown in FIGS. 7 and 8 is suitable for use in situations where the reactor 110 is fitted with a stirrer (not shown).

In FIG. 7, a gaseous components outlet leading from a head space zone 107 is shown and indicated by reference numeral 26.

Figure 9:
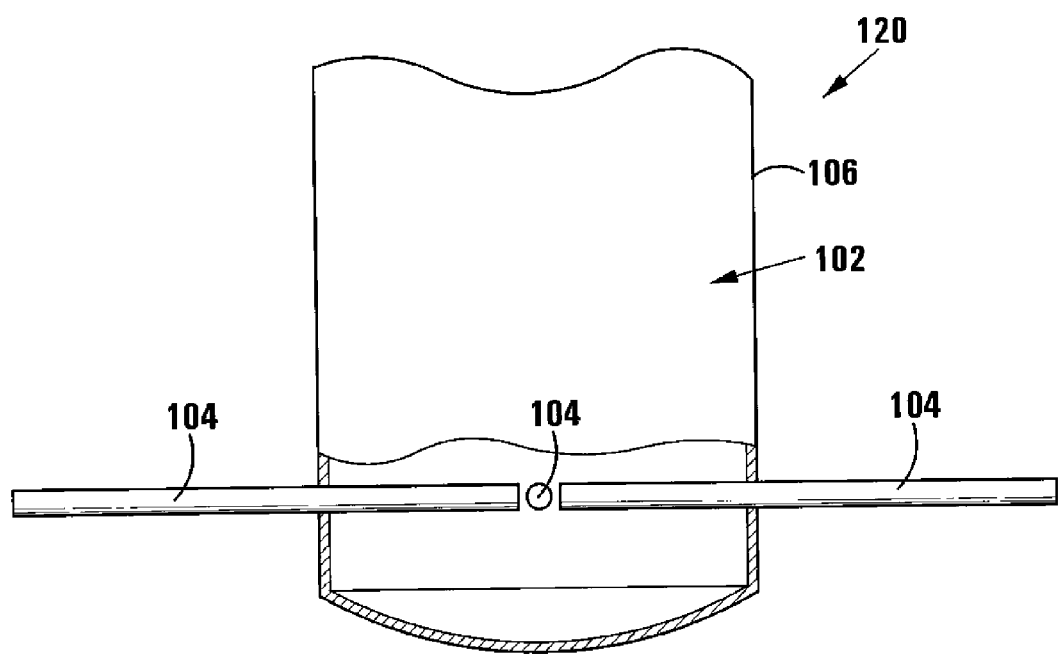
FIG. 9 shows a partially sectioned elevational view of a bottom portion of another embodiment of a hydrocarbon oligomerisation reactor in accordance with the invention.

Referring to FIG. 9, another embodiment of an oligomerisation reactor in accordance with the invention is generally indicated by reference numeral 120. The reactor 120 is similar to the reactor 100 and unless otherwise indicated, the same or similar parts or features are indicated by the same reference numerals.

In the reactor 120, the nozzles 104 are aimed at each other. The nozzles 104 are arranged in two pairs of diagonally opposed nozzles. With this arrangement, a volume of bulk liquid phase with high localised turbulence in use surrounds the inlet nozzles 104. Being located in a volume of localised turbulence, the nozzles 104 are less prone to fouling and are in effect self-cleaning.

The reactors 110, 120 can be used in the process 10, 50 as the reactors 12, 12.1 and 12.2 shown in FIGS. 1 and 2.

Figure 3:
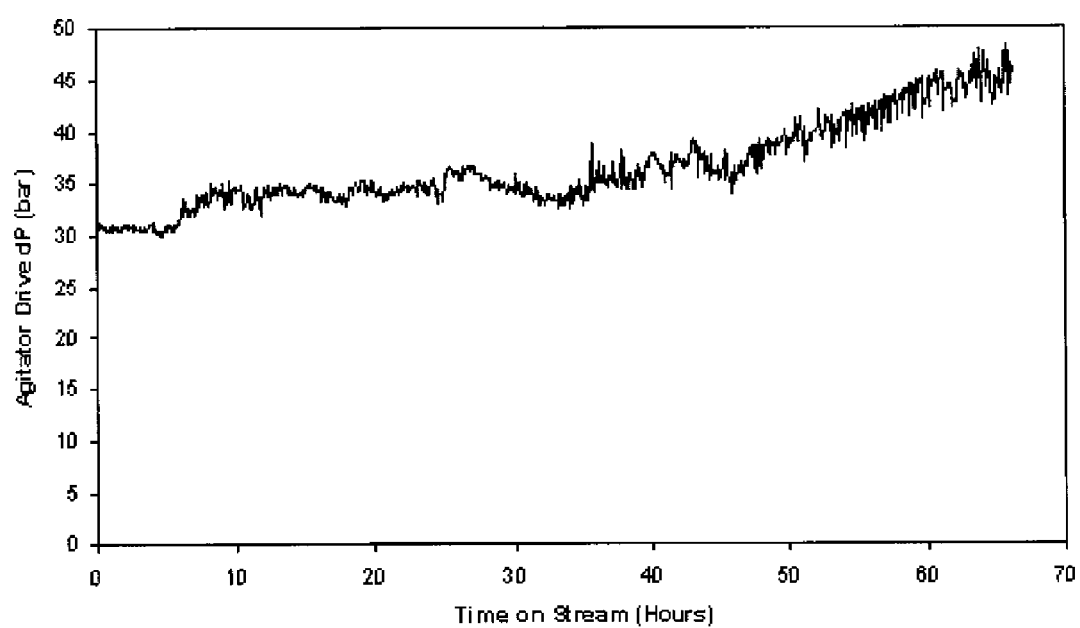
FIG. 3 shows a graph of the load on an agitator, represented by hydraulic drive pump differential pressure, in a pilot plant reactor subjected to fouling caused by the precipitation of polymer on the agitator.
Figure 4:
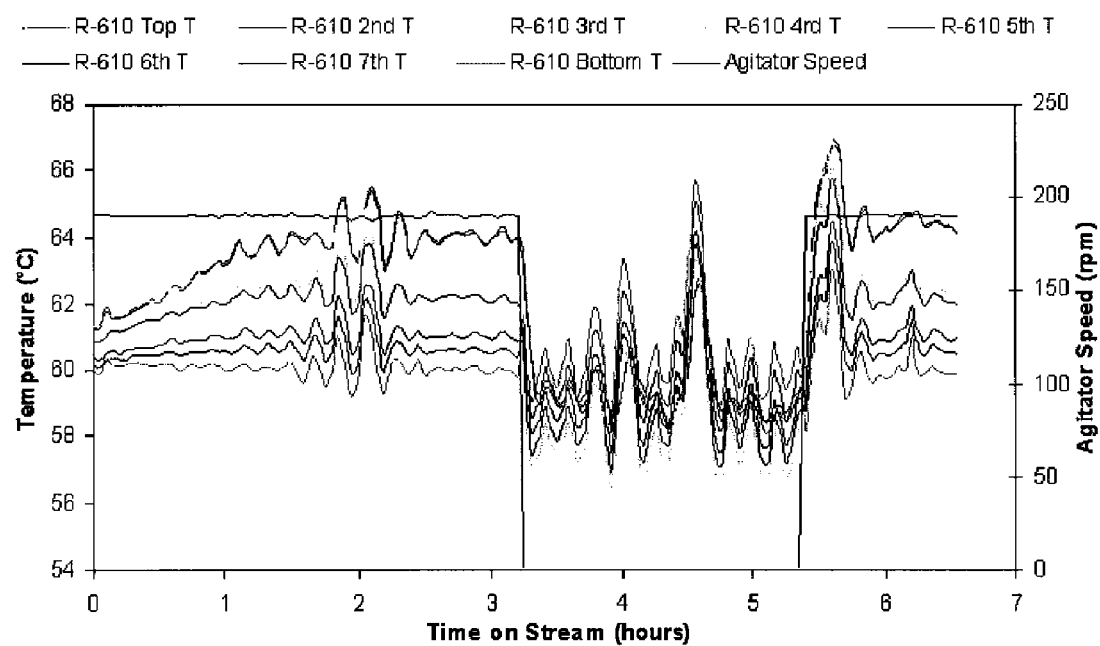
FIG. 4 shows graphs of axial pilot plant reactor temperature profile and agitator speed, for the pilot plant reactor of FIG. 3.

The Applicant believes that the process 10, 50 and the reactors 100,110, 120 as illustrated, are less subject to the risk of fouling, compared to conventional processes and reactors for polymerising or oligomerising a hydrocarbon. This risk of fouling, for conventional polymerisation or oligomerisation processes and apparatus, particularly those including an agitator in the reactor, is a significant problem, with the present invention going a long way to addressing this problem. FIG. 3 illustrates the increased load on an agitator with time on stream under reaction conditions due to precipitation of polymer on the agitator of a pilot plant reactor making use of an hydraulic drive. Liquid ethylene was used as a feed. As will be noted, the hydraulic drive pump differential pressure increases with increasing load to maintain the agitator at a target speed. This increased load is caused by fouling of the agitator. FIG. 4 shows that switching off the agitator of said pilot plant reactor is not detrimental to the axial reactor temperature profile in said pilot plant reactor. Although there is a temperature oscillation when the agitator is switched off, caused by non-optimised control tuning, it will be noted that the temperature profile of each of the axially located thermocouples is consistent with the others and remains within a tight temperature tolerance.

The invention claimed is:

1. A process for polymerizing or oligomerising a hydrocarbon, the process comprising the steps of:
    feeding a liquid hydrocarbon reactant into a bulk liquid phase comprising polymeric or oligomeric product admixed with a catalyst, the liquid hydrocarbon reactant having a boiling temperature lower than a bulk temperature of the bulk liquid phase;
    allowing the liquid hydrocarbon reactant to vaporise to form bubbles rising through the bulk liquid phase and to polymerise or oligomerise to form the polymeric or oligomeric product, with the rising bubbles creating turbulence in the bulk liquid phase, thereby mixing the bulk liquid phase;
    allowing gaseous components comprising any unreacted vapourised hydrocarbon reactant and any gaseous product that may have formed to disengage from the bulk liquid phase into a head space above the bulk liquid phase;
    withdrawing the gaseous components from the head space;
    cooling the gaseous components withdrawn from the head space;
    forming condensed hydrocarbon reactant and gaseous product;
    separating the condensed hydrocarbon reactant from the gaseous product;
    recycling the condensed hydrocarbon reactant in liquid form to the bulk liquid phase; and
    withdrawing the bulk liquid phase which includes polymeric or oligomeric product from the bulk liquid phase.

2. The process as claimed in claim 1, in which the bulk liquid phase includes an inert solvent acting as a diluent thereby limiting incorporation of desirable oligomeric product in heavier by-products, the process including treating the withdrawn liquid phase to separate polymeric or oligomeric product from solvent by subjecting the withdrawn liquid phase to at least one distillation stage to obtain a solvent stream.

3. The process as claimed in claim 1, which includes treating the gaseous product in at least one distillation stage operating at a lower pressure than the pressure at which the bulk liquid phase is maintained to recover uncondensed unreacted hydrocarbon reactant from the gaseous product, producing the hydrocarbon reactant in liquid form.

4. The process as claimed in claim 1, in which the polymerisation or oligomerisation reaction or reactions in the bulk liquid phase are exothermic, and in which sufficient liquid hydrocarbon reactant is fed to the bulk liquid phase to balance the reaction exotherm, thereby approaching isothermal behaviour.

5. The process as claimed in claim 1, in which the liquid hydrocarbon reactant is an olefins feedstock comprising one or more olefinic monomers.

6. The process as claimed in claim 5, in which the liquid hydrocarbon reactant is liquid ethylene.

7. The process as claimed in claim 1, in which the bulk liquid phase is in the form of a bubbling column and which includes feeding liquid phase withdrawn from the bulk liquid phase to a further bubbling column of said bulk liquid phase, and feeding said liquid hydrocarbon reactant also to said further bubbling column, to form further polymeric or oligomeric product, the process thus using at least two bubbling columns of bulk liquid phase in series, with fresh liquid hydrocarbon reactant being fed into each bubbling column.

8. The process as claimed in claim 1, which includes combining a gaseous hydrocarbon reactant feed with the gaseous components withdrawn from the head space, so that the gaseous hydrocarbon feed is condensed with the condensed hydrocarbon reactant and fed with the recycled condensed hydrocarbon reactant to the bulk liquid phase as the liquid hydrocarbon reactant.

9. The process as claimed in claim 1, in which the liquid hydrocarbon reactant is impinged on an impingement surface provided in a reactor holding the bulk liquid phase, or on another feed stream entering the reactor, to create at least a localised area of high turbulence in the bulk liquid phase.

10. The process as claimed in claim 9, in which the liquid hydrocarbon reactant is impinged against an impingement surface defined by a wall of the reactor and/or against an impingement formation provided inside the reactor, defining an impingement surface.

11. The process as claimed in claim 10, in which the liquid hydrocarbon reactant is fed into the bulk liquid phase through at least one nozzle aimed at the impingement surface.

12. Hydrocarbon polymerisation or oligomerisation apparatus comprising:
a reactor vessel defining a liquid phase zone below a head space zone for holding a bulk liquid phase comprising polymeric or oligomeric product in the liquid phase zone;
a hydrocarbon reactant inlet at or near a bottom of the reactor vessel leading into the liquid phase zone, the inlet having at least one hydrocarbon reactant inlet nozzle aimed at an impingement surface provided inside, or defining, the liquid phase zone such that in use a localised area of high turbulence is created by the injection of a hydrocarbon reactant through the hydrocarbon reactant inlet nozzle onto the impingement surface, or said at least one hydrocarbon reactant inlet nozzle being aimed at another fluid stream inlet nozzle so that in use a localised area of high turbulence is created by the injection of a hydrocarbon reactant through said at least one hydrocarbon reactant inlet nozzle into impinging contact with a fluid stream being injected through said another fluid stream inlet nozzle;
a gaseous components outlet leading from the head space zone in use through which gaseous components collecting in the head space zone are withdrawn;
a condenser in flow communication with the gaseous components outlet; and
a separator in flow communication with the condenser and with the reactor vessel so that, in use, gaseous components withdrawn from the head space are cooled in the condenser to condense hydrocarbon reactant with the condensed hydrocarbon reactant being separated from uncondensed gaseous components in the separator and returned to the reactor vessel.

13. The apparatus as claimed in claim 12, in which the impingement surface is defined by a wall of the reactor vessel and/or by an impingement formation provided as an internal inside the liquid phase zone.

14. The apparatus as claimed in claim 12, which is characterised by the absence of a mechanical stirrer or agitator.

15. Hydrocarbon polymerisation or oligomerisation apparatus which includes:
a reactor vessel defining a liquid phase zone below a head space zone to hold a bulk liquid phase comprising polymeric or oligomeric product in the liquid phase zone;
a liquid hydrocarbon reactant inlet at or near the bottom of the reactor vessel leading into the liquid phase zone, the liquid hydrocarbon reactant inlet having at least one liquid hydrocarbon reactant inlet nozzle inside the liquid phase zone aimed at an impingement surface provided inside, or defining, the liquid phase zone such that in use a localised area of high turbulence is created inside the liquid phase zone by the injection of a liquid hydrocarbon reactant through the liquid hydrocarbon reactant inlet nozzle onto the impingement surface of the liquid phase zone; and
a gaseous components outlet leading from the head space zone in use through which gaseous components collecting in the head space zone are withdrawn
a condenser in flow communication with the gaseous components outlet; and
a separator in flow communication with the condenser and with the reactor vessel so that, in use, gaseous components withdrawn from the head space are cooled in the condenser to condense hydrocarbon reactant with the condensed hydrocarbon reactant being separated from uncondensed gaseous components in the separator and returned to the reactor vessel.

16. Hydrocarbon polymerisation or oligomerisation apparatus which includes:
a reactor vessel defining a liquid phase zone below a head space zone to hold a bulk liquid phase comprising polymeric or oligomeric product in the liquid phase zone;
a liquid hydrocarbon reactant inlet at or near the bottom of the reactor vessel leading into the liquid phase zone, the liquid hydrocarbon reactant inlet having at least one liquid hydrocarbon reactant inlet nozzle inside the liquid phase zone aimed at another fluid stream inlet nozzle inside the liquid phase zone so that in use a localised area of high turbulence is created inside the liquid phase zone by the injection of a liquid hydrocarbon reactant into the liquid phase zone through said at least one liquid hydrocarbon reactant inlet nozzle into impinging contact with a fluid stream being injected into the liquid phase zone through said another fluid stream inlet nozzle; and
a gaseous components outlet leading from the head space zone in use through which gaseous components collecting in the head space zone are withdrawn a condenser in flow communication with the gaseous components outlet; and a separator in flow communication with the condenser and with the reactor vessel so that, in use, gaseous components withdrawn from the head space are cooled in the condenser to condense hydrocarbon reactant with the condensed hydrocarbon reactant being separated from uncondensed gaseous components in the separator and returned to the reactor vessel.

* * * * *